United States Patent
Katsunuma et al.

(10) Patent No.: US 11,969,575 B2
(45) Date of Patent: Apr. 30, 2024

(54) MEDICAL INFUSION PUMP, METHOD OF CONTROLLING MEDICAL INFUSION PUMP, AND MEDICAL INFUSION PUMP SYSTEM

(71) Applicant: TERUMO KABUSHIKI KAISHA, Tokyo (JP)

(72) Inventors: Takayuki Katsunuma, Yokohama (JP); Takafumi Nomura, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 115 days.

(21) Appl. No.: 17/725,277

(22) Filed: Apr. 20, 2022

(65) Prior Publication Data

US 2022/0241496 A1    Aug. 4, 2022

Related U.S. Application Data

(63) Continuation of application No. PCT/JP2020/038755, filed on Oct. 14, 2020.

(30) Foreign Application Priority Data

Oct. 29, 2019  (JP) .................. 2019-196702

(51) Int. Cl.
*A61M 5/145*  (2006.01)
*G06K 7/10*   (2006.01)
(Continued)

(52) U.S. Cl.
CPC ..... *A61M 5/14546* (2013.01); *G06K 7/10366* (2013.01); *G16H 20/17* (2018.01);
(Continued)

(58) Field of Classification Search
None
See application file for complete search history.

(56) References Cited

U.S. PATENT DOCUMENTS 9,498,131 B1 * 11/2016 Allen ................... A61B 5/4205
10,089,055 B1   10/2018 Fryman
(Continued)

FOREIGN PATENT DOCUMENTS

CN        101219087 A    7/2008
JP        2008-080036 A  4/2008
(Continued)

OTHER PUBLICATIONS

Extended European Search Report issued in connection with EP Appl. Ser. No. 20882446.6 dated Nov. 4, 2022.
(Continued)

*Primary Examiner* — K. Wong
(74) *Attorney, Agent, or Firm* — Foley & Lardner LLP

(57) ABSTRACT

A medical infusion pump includes: a reader configured to read identification information stored in an RF tag by wireless communication; and a control unit configured to set information about administration of a drug based on the identification information read from the RF tag. In a case in which the reader reads two different pieces of the identification information, the control unit selects only one piece of the identification information out of the two different pieces of the identification information and sets the information about administration based on said one piece of the identification information.

16 Claims, 12 Drawing Sheets

(51) Int. Cl.
    *G16H 20/17*     (2018.01)
    *A61M 5/142*     (2006.01)

(52) U.S. Cl.
    CPC ............. *A61M 2005/14208* (2013.01); *A61M 2205/3584* (2013.01); *A61M 2205/6054* (2013.01)

(56) References Cited

U.S. PATENT DOCUMENTS

| | | | |
|---|---|---|---|
| 11,235,100 B2 * | 2/2022 | Howard | G16H 70/40 |
| 11,399,721 B2 * | 8/2022 | Mahalingam | G09B 5/02 |
| 2003/0106553 A1 * | 6/2003 | Vanderveen | G16H 20/17 |
| | | | 128/204.23 |
| 2003/0139701 A1 | 7/2003 | White et al. | |
| 2015/0001285 A1 * | 1/2015 | Halbert | G16H 20/17 |
| | | | 235/375 |

FOREIGN PATENT DOCUMENTS

| | | |
|---|---|---|
| JP | 2012-005756 A | 1/2012 |
| JP | 2012-179099 A | 9/2012 |
| WO | WO-2006/086735 A2 | 8/2006 |
| WO | WO-2019/064903 A1 | 4/2019 |
| WO | WO-2019/064952 A1 | 4/2019 |
| WO | WO-2019/187689 A1 | 10/2019 |

OTHER PUBLICATIONS

Chinese Office Action issued in connection with CN Appl. Ser. No. 202080073545.9, dated Mar. 2, 2023.

International Searching Authority, "International Search Report," issued in connection with International Patent Application No. PCT/JP2020/038755, dated Dec. 1, 2020.

International Searching Authority, "Written Opinion," issued in connection with International Patent Application No. PCT/JP2020/038755, dated Dec. 1, 2020.

* cited by examiner

MEDICAL INFUSION PUMP, METHOD OF CONTROLLING MEDICAL INFUSION PUMP, AND MEDICAL INFUSION PUMP SYSTEM

CROSS-REFERENCE TO RELATED APPLICATIONS

This is a bypass continuation of PCT Patent Application No. PCT/JP2020/038755, filed on Oct. 14, 2020, which claims priority to Japanese Patent Application No. 2019-196702, filed on Oct. 29, 2019. The contents of these applications are hereby incorporated by reference in their entireties.

BACKGROUND

The present disclosure relates to a medical infusion pump, a method of controlling the medical infusion pump, and a medical infusion pump system.

Medical infusion pumps such as a syringe pump and an infusion pump are used, for example, in an operating room, an intensive care unit (ICU), and the like. The medical infusion pump is used, for example, when a drug such as an anticancer drug, an anesthetic, a chemotherapeutic agent, or a nutrient is administered to a patient for a relatively long time with high accuracy.

In order to suppress administration of a drug with an incorrect setting when the drug is administered by a medical infusion pump, a method of using a drug library is known (see, for example, Japanese Patent Pub. No. 2012-179099 A). The drug library is, for example, a database of setting information and the like at the time of administration of each of several thousand kinds of drugs. In the drug library, each drug has drug-specific setting information such as a reference administration rate, an upper limit value/a lower limit value of the administration rate, a drug code, and a drug color.

In addition, a method has been proposed in which a drug library is stored in a medical infusion pump, and a drug is administered according to drug-specific setting information using a radio frequency (RF) tag attached to a syringe or the like filled with the drug (see, for example, PCT Pub. No. WO 2019/064903 A). In this case, the medical infusion pump reads the drug identification information stored in the RF tag, and the information about administration of the drug such as the administration rate is set on the basis of the drug-specific setting information corresponding to the drug identification information. The drug identification information is information that can identify a drug, and is, for example, a drug code.

By using the RF tag, in a medical institution such as a hospital, it is possible to automate and speed up acquisition of setting information corresponding to a drug stored in a syringe container, an infusion container, or the like used for a medical infusion pump. In addition, by using the RF tag, it can be expected to suppress erroneous administration of a drug due to an artificial error. Therefore, use of the RF tag in the medical infusion pump is expected in the future.

SUMMARY

The drug used in the medical infusion pump may be provided from a pharmaceutical manufacturer as a prefilled syringe or the like in which a syringe container is filled with the drug in advance. In the future, it is assumed that an RF tag is attached to the prefilled syringe in a factory of a drug manufacturer for the purpose of distribution management. As the RF tag for logistics management, for example, a standard code capable of uniquely identifying each article worldwide, such as a serialized global trade item number (SGTIN), is considered to be used.

On the other hand, it is assumed that an RF tag intended for drug authentication in a medical institution is attached to a syringe container, an infusion container, and the like used in a medical infusion pump in the future. An object of the RF tag for drug authentication is to suppress erroneous administration of a drug or the like. As the RF tag for drug authentication, it is assumed that a unique code of a medical institution associated with prescription information for a patient is used. In the present disclosure, the standard code and the unique code acquired from the RF tag are information for identifying a drug with which a drug storage container such as a syringe container or an infusion container to which the RF tag is attached is filled, and thus are referred to as identification information.

However, when two RF tags of an RF tag for logistics management and an RF tag for drug authentication are attached to one syringe container or one infusion container, two pieces of identification information may be read when the medical infusion pump reads these RF tags. In a case in which the two pieces of identification information are read, it is necessary to clarify to which identification information the medical infusion pump sets the information about administration of the drug according.

An object of the present disclosure made in view of such a point is to provide a medical infusion pump, a method of controlling a medical infusion pump, and a medical infusion pump system capable of appropriately administering a drug in a case in which a plurality of pieces of identification information is read.

According to a first aspect, a medical infusion pump includes a reader capable of reading identification information stored in an RF tag by wireless communication and a control unit that sets information about administration of a drug on the basis of the identification information read from the RF tag. In a case in which the reader reads two different pieces of the identification information, the control unit selects only one piece of the identification information out of the two different pieces of the identification information and sets the information about administration.

According to one embodiment, the RF tag is attached to a drug storage container that contains the drug.

According to one embodiment, the drug storage container is a syringe.

According to one embodiment, in a case in which the reader reads two different pieces of the identification information, the control unit selects only the one piece of identification information on the basis of data of a predetermined region included in each piece of the identification information.

According to one embodiment, in a case in which the reader reads two pieces of the same identification information, the control unit does not set the information about administration.

According to one embodiment, in a case in which the reader reads three or more pieces of the identification information, the control unit does not set the information about administration.

According to one embodiment, in a case in which the reader reads only the one piece of identification information, the control unit sets the information about administration on the basis of the read one piece of the identification information.

According to one embodiment, the medical infusion pump further includes a display unit that displays the information about administration.

According to one embodiment, the identification information includes a first type of identification information and a second type of identification information having different data structures. The control unit selects only the second type of identification information when one of the two pieces of the different identification information is the first type of identification information and the other is the second type of identification information.

According to one embodiment, the first type of identification information is identification information allocated to the drug, and the second type of identification information is identification information associated with prescription information for administering the drug.

According to one embodiment, the control unit sets at least part of the prescription information as the information about administration in a case in which the identification information includes the second type of identification information.

According to one embodiment, the medical infusion pump further includes a communication unit that communicates with a server, and the control unit acquires the prescription information stored in association with the second type of the identification information from the server via the communication unit.

According to one embodiment, the first type of identification information is identification information uniquely defined according to a standard. The second type of identification information is identification information uniquely set by a medical institution.

According to another aspect, a method of controlling a medical infusion pump includes reading identification information stored in an RF tag by wireless communication, and setting information about administration of a drug on the basis of the identification information read from the RF tag. This control method includes, in a case in which two pieces of the different identification information are read, selecting only one piece of the identification information out of the two pieces of different identification information, and setting the information about administration.

According to one embodiment, a medical infusion pump system includes a drug storage container to which an RF tag is attached and a medical infusion pump. The drug storage container contains a drug to be administered to a patient. The medical infusion pump includes a reader capable of reading identification information stored in the RF tag by wireless communication, and a control unit that sets information about administration of a drug on the basis of the identification information read from the RF tag. In a case in which the reader reads two different pieces of the identification information, the control unit selects only one piece of the identification information out of the two different pieces of the identification information and sets the information about administration.

As one embodiment of the present disclosure, a server is further included, and the medical infusion pump further includes a communication unit that communicates with the server. The identification information includes first type of identification information and second type of identification information. The server stores information stored in association with the second type of identification information. The control unit selects only the second type of identification information when one of the two pieces of the different identification information is the first type of identification information and the other is the second type of identification information. The control unit acquires the information stored in association with the second type of the identification information from the server via the communication unit, and sets the information about administration.

According to the medical infusion pump, the method of controlling the medical infusion pump, and the medical infusion pump system according to the present disclosure, it is possible to appropriately set information about administration of a drug in a case in which a plurality of pieces of identification information is read.

DETAILED DESCRIPTION

Figure 1:
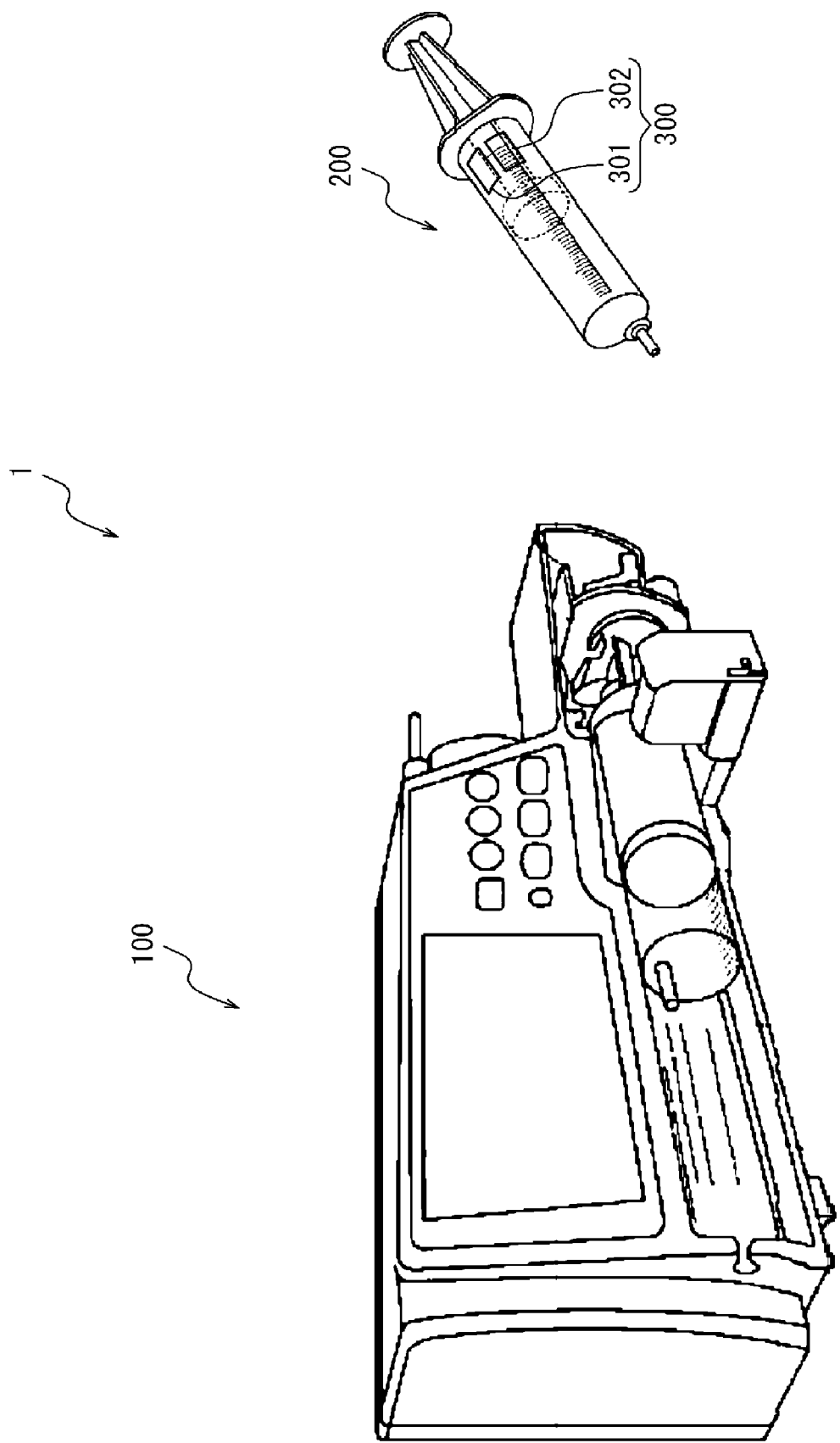
FIG. 1 is a schematic configuration diagram of a medical infusion pump system according to an embodiment of the present disclosure.

Embodiments of the present disclosure will be described below with reference to the drawings. The dimensional ratios in the drawings may be exaggerated and different from actual ratios, for convenience of description. In the drawings, the same members are denoted by the same reference numerals.

Overview of In-Medical Institution System Including Medical Infusion Pump System FIG. 1 is a schematic configuration diagram of a medical infusion pump system 1 according to an embodiment of the present disclosure. The medical infusion pump system 1 includes a medical infusion pump 100 and a syringe 200. The syringe 200 can be attached to the medical infusion pump 100. One or more RF tags 300 are attached to the syringe 200. In the illustrated example, the one or more RF tags 300 include a first RF tag 301 and a second RF tag 302.

The RF tag 300 is a small electronic device capable of wirelessly reading information. The RF tag 300 can receive an electromagnetic wave from the outside to transmit at least identification information (ID information). The identification information is information that can identify a drug in the syringe 200 to which the individual RF tag 300 is attached. In the present application, the RF tag 300 is synonymous with a radio frequency identifier (RFID), a radio tag, and an integrated circuit (IC) tag. The medical infusion pump 100 and the RF tag 300 can communicate with each other by wireless communication using a frequency in an ultra high frequency (UHF) band or a high frequency (HF) band, for example. For example, the RF tag 300 may employ an RF tag conforming to the ISO/IEC 18000-63 standard. The RF tag 300 is not limited to an RF tag conforming to the ISO/IEC 18000-63 standard.

In an embodiment of the present disclosure, the first RF tag 301 is an RF tag that adopts a standard code used for distribution management and the like. In the present embodiment, the standard code is the first type of identification information. The standard code includes, for example, SGTIN. The SGTIN includes a company code for identifying a company, a product code for identifying a product, and a serial number for each product. Therefore, the standard code includes drug identification information identifying a drug. In a case in which the syringe 200 is a prefilled syringe, the first RF tag 301 can be attached to a factory or the like of a manufacturer who manufactures the prefilled syringe. The standard code is an example of the first type of identification information. The first type of identification information is not limited to the standard code.

The second RF tag 302 may be an RF tag that is attached for the purpose of drug authentication or the like in a medical institution and employs a medical institution's unique code (unique code). In the present embodiment, the unique code of the medical institution is the second type of identification information. As the unique code, a prescription ID to a patient in a medical institution or a code associated with the prescription ID may be used. Here, the prescription ID is identification information assigned to prescription information that is an instruction of a method of administering a drug to a patient by a doctor. The second RF tag 302 is issued when a drug is dispensed or prepared in a medical institution, and can be attached to a drug container such as the syringe 200. The unique code of the medical institution is an example of the second type of identification information. The second type of identification information is not limited to the unique code of the medical institution.

The intensity of the electromagnetic wave transmitted from the medical infusion pump 100 to the RF tag 300 is limited to a predetermined intensity or less. The predetermined intensity is an intensity that can be received by the RF tag 300 when the syringe 200 is attached to the medical infusion pump 100 but cannot be received by the RF tag 300 when the syringe 200 is away from the medical infusion pump 100 by a predetermined distance or more. As a result, it is possible to inhibit the medical infusion pump 100 from erroneously reading data from the RF tag 300 attached to the syringe 200 not attached to the medical infusion pump 100.

The medical infusion pump 100 may store a drug library. The drug library is, for example, a database of drug-specific setting information and the like at the time of administration for each of several thousand kinds of drugs. In the drug library, each drug has setting information such as a reference administration rate, an upper limit value/a lower limit value of the administration rate, a drug code, and a drug color. Hereinafter, a collection of a plurality of pieces of setting information for one drug is also referred to as a "drug profile". The drug library may be stored not in the medical infusion pump 100 but in a server 410 in a medical institution to be described later. In this case, the medical infusion pump 100 may be configured to appropriately acquire necessary setting information from the drug library stored in the server 410.

Figure 2:
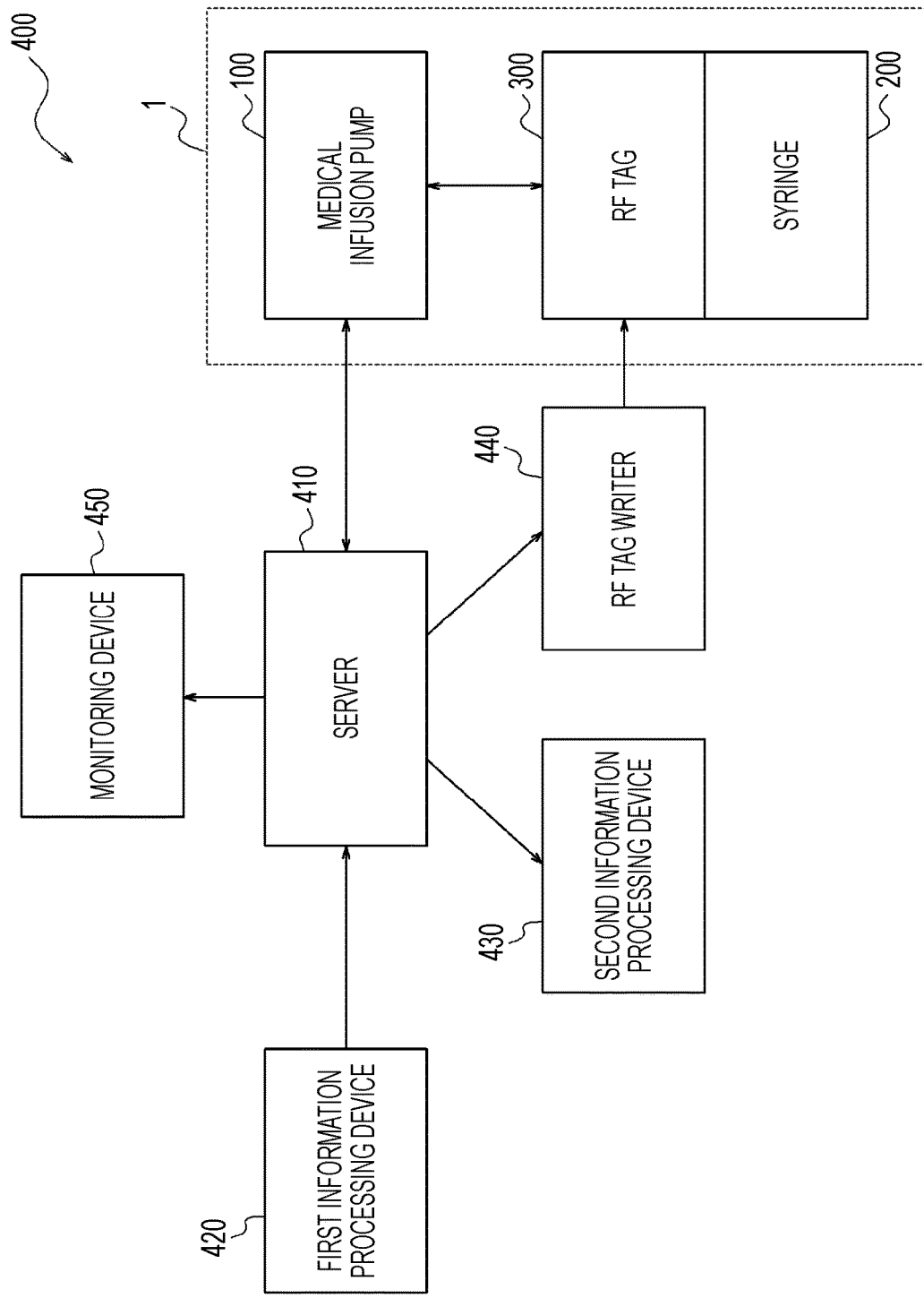
FIG. 2 is a diagram illustrating an example of an in-medical institution system including the medical infusion pump system of FIG. 1.

FIG. 2 is a diagram illustrating an example of an in-medical institution system 400 including the medical infusion pump system 1 of FIG. 1. The in-medical institution system 400 includes the medical infusion pump system 1, the server 410, a first information processing device 420, a second information processing device 430, and an RF tag writer 440. The in-medical institution system 400 may further include a monitoring device 450. The components included in the in-medical institution system 400 are not limited to these units, and various devices can be connected.

The server 410 is a device that manages prescription information associated with each patient. The prescription information includes information about administration of the drug to the patient. The prescription information may include information such as information identifying a patient (hereinafter referred to as "patient identification information"), drug identification information, and a dose of a drug, an administration rate, and an administration time. The server 410 issues a unique code for each prescription information, and manages the unique code and the prescription information in association with each other. The unique code may be a non-duplicate number in a medical institution. In addition, the server 410 may store the drug library as described above. The medical infusion pump 100 can be configured to be able to appropriately acquire necessary information from the server 410. The medical infusion pump system 1 may include the server 410 in addition to the medical infusion pump 100, the syringe 200, and the RF tag 300.

The server 410 can receive operation information from the medical infusion pump 100 during an operation of the medical infusion pump 100. The operation information is information including states such as an operation start, an operation end, a normal operation, an administration rate, an amount of administered drug, and occurrence of abnormality of the medical infusion pump 100. The server 410 can display the operation information about the monitoring device 450.

The first information processing device 420 is a device to which a doctor and a nurse or the like who has received an instruction from the doctor input prescription information. The first information processing device 420 is, for example, an information processing terminal such as a personal computer used by each doctor. One unique code is issued and associated with a set of prescription information input from the first information processing device 420 in the server 410.

The second information processing device 430 is a device that instructs and manages dispensing and preparation of a drug on the basis of prescription information. A medical worker such as a pharmacist dispenses and prepares a drug in accordance with an instruction from the second information processing device 430. There are a case in which a drug is dispensed in a state where a container is filled with the drug in advance like a prefilled syringe, and a case in which a drug is prepared in a medical institution according to prescription information and a container is filled with the drug. In some cases, the first RF tag 301 including a standard code that is the first type of identification information is attached to the prefilled syringe in advance for distribution management. The first type of identification information is unique identification information assigned to a drug as an article.

The RF tag writer 440 is a device that issues the second RF tag 302 in conjunction with the second information processing device 430. The RF tag writer 440 can write data in a memory 330, which will be described later, of the second RF tag 302 before writing data prepared in advance. The RF tag writer 440 writes, for example, a unique code that is the second type of identification information in the second RF tag 302. The unique code is, for example, a prescription ID. The second RF tag 302 issued by the RF tag writer 440 is attached to the syringe 200 including a prefilled syringe and a drug storage container that contains a drug such as an infusion container. One face of the second RF tag 302 issued by the RF tag writer 440 may be an adhesive seal. The second RF tag 302 can be attached to the syringe 200 by attaching a face of an adhesive seal to the syringe 200.

The monitoring device 450 is a device that is located at a position different from the medical infusion pump 100 and displays the operation state of the medical infusion pump 100. For example, the monitoring device 450 may be disposed in a nurse station or the like where a nurse is resident. The nurse or the like can monitor the operation state of the medical infusion pump 100 by the monitoring device 450.

Configuration of Medical Infusion Pump System

Figure 3:
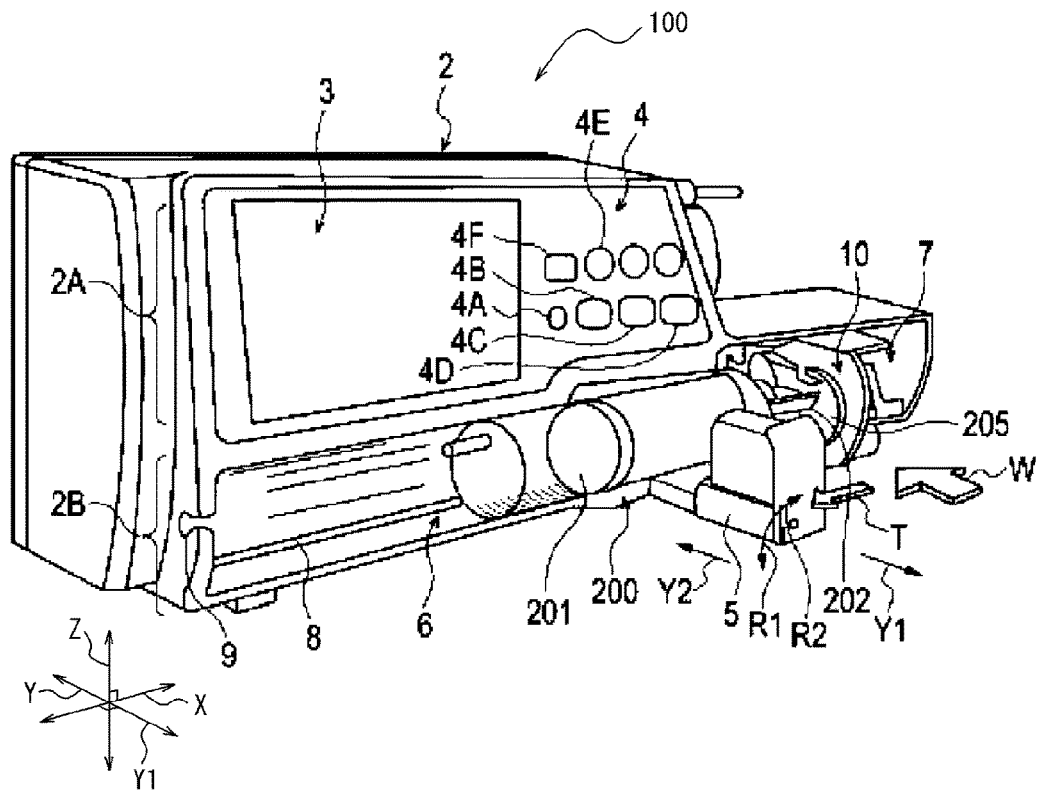
FIG. 3 is a schematic perspective view illustrating the medical infusion pump of FIG. 1 in a state where a syringe is attached.
Figure 4:
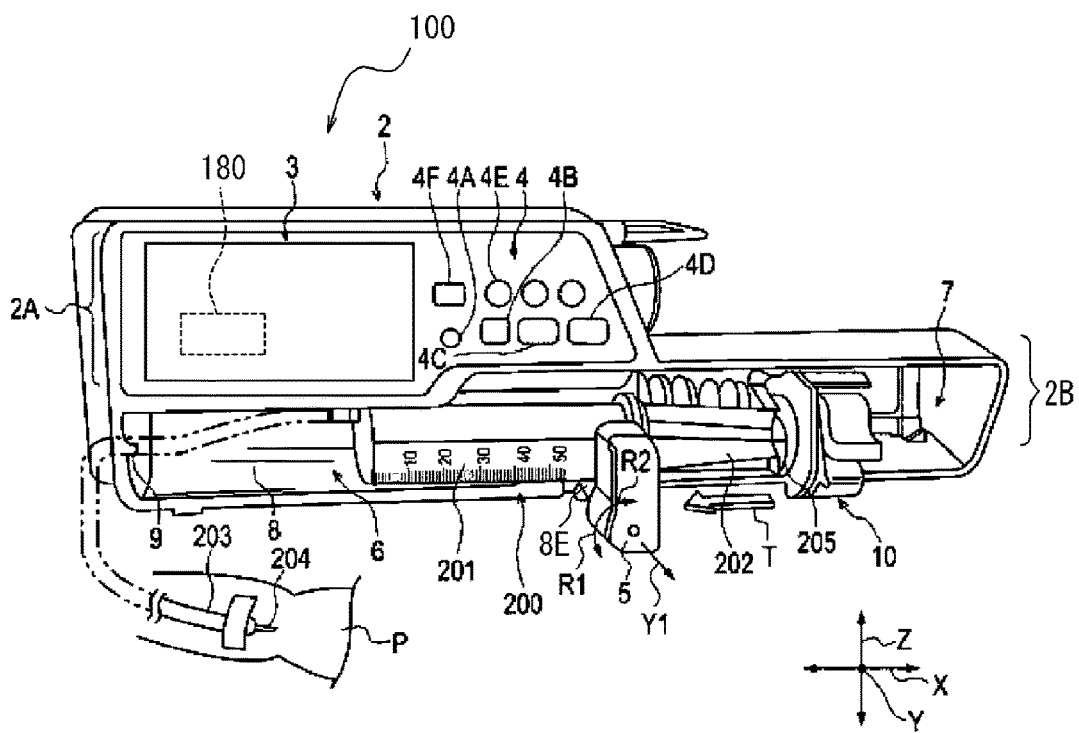
FIG. 4 is a schematic front view of the medical infusion pump illustrated in FIG. 3.

Next, each component of the medical infusion pump system 1 will be described in detail. FIG. 3 is a schematic perspective view of the medical infusion pump 100 according to an embodiment of the present disclosure. FIG. 4 is a schematic front view of the medical infusion pump 100 according to an embodiment of the present disclosure. In FIGS. 3 and 4, as an example, a case in which the medical infusion pump 100 is a syringe pump is illustrated.

The medical infusion pump 100 is used, for example, in an operating room, and an intensive care unit such as an intensive care unit (ICU), a coronary care unit (CCU), or a neonatal intensive care unit (NICU), for continuously delivering various drugs including an intravenous anesthetic, a vasoactive agent, and the like with which the syringe 200 is filled into the body of a patient. The intravenous anesthetic includes a drug that acts on the nervous system to exert a sedative effect and/or an analgesic effect.

The medical infusion pump 100 can deliver various drugs including an intravenous anesthetic, a vasoactive agent, and the like with which the syringe 200 is filled into the body of the patient. Examples of applicable intravenous anesthetics include propofol, midazolam, and remifentanil. Examples of applicable vasoactive agents include epinephrine, noradrenaline, dobutamine, dopamine, isosorbide nitrate, and nitroglycerin.

As illustrated in FIGS. 3 and 4, the medical infusion pump 100 presses a syringe pusher 202 of the syringe 200 as the drug storage container filled with the drug in the T direction, and accurately feeds the drug in a syringe body 201 to a patient P via a tube 203 and an indwelling needle 204. At this time, the syringe body 201 of the syringe 200 is set so as not to move by a clamp 5 with respect to the medical infusion pump 100.

The medical infusion pump 100 includes a main body cover 2.

The main body cover 2 is integrally molded with a molded resin material having chemical resistance. Thus, the main body cover 2 has a splash-proof processing structure. The splash-proof processing structure can suppress entry of a drug or the like into the medical infusion pump 100 even if the drug or the like is applied to the medical infusion pump 100. The reason why the splash-proof processing structure is provided is that a drug in the syringe body 201 may spill, a drip solution disposed above the medical infusion pump 100 may spill, or a disinfectant solution or the like used in the periphery may scatter and adhere.

As illustrated in FIGS. 3 and 4, the main body cover 2 has an upper portion 2A and a lower portion 2B.

A display unit 3 and an operation panel unit 4 are disposed in the upper portion 2A.

In the lower portion 2B, a syringe installation unit 6 and a syringe pusher drive unit 7 for pushing the syringe pusher 202 are disposed.

The display unit 3 is an image display device capable of performing color display. The display unit 3 can be, for example, a color liquid crystal display device. The display unit 3 can display not only information in Japanese but also information in a plurality of foreign languages as necessary. The display unit 3 is disposed at an upper left position of the upper portion 2A of the main body cover 2 and above the syringe installation unit 6 and the syringe pusher drive unit 7. The display unit 3 may include an input device such as a touch sensor and receive an input from the user.

The operation panel unit 4 is disposed on the right side of the display unit 3 in the upper portion 2A of the main body cover 2. A power ON/OFF button 4A, an operation indicator 4F, and an operation button are disposed on the operation panel unit 4. FIGS. 3 and 4 illustrate an example in which a fast delivery switch button 4B, a start switch button 4C, a stop switch button 4D, and a menu selection button 4E are disposed as the operation buttons.

As illustrated in FIGS. 3 and 4, the syringe installation unit 6 and the syringe pusher drive unit 7 are disposed side by side along the X direction. The syringe installation unit 6 can detachably fit and fix the syringe 200. The syringe installation unit 6 can fix a plurality of types of syringes 200 having different sizes.

Figure 5:
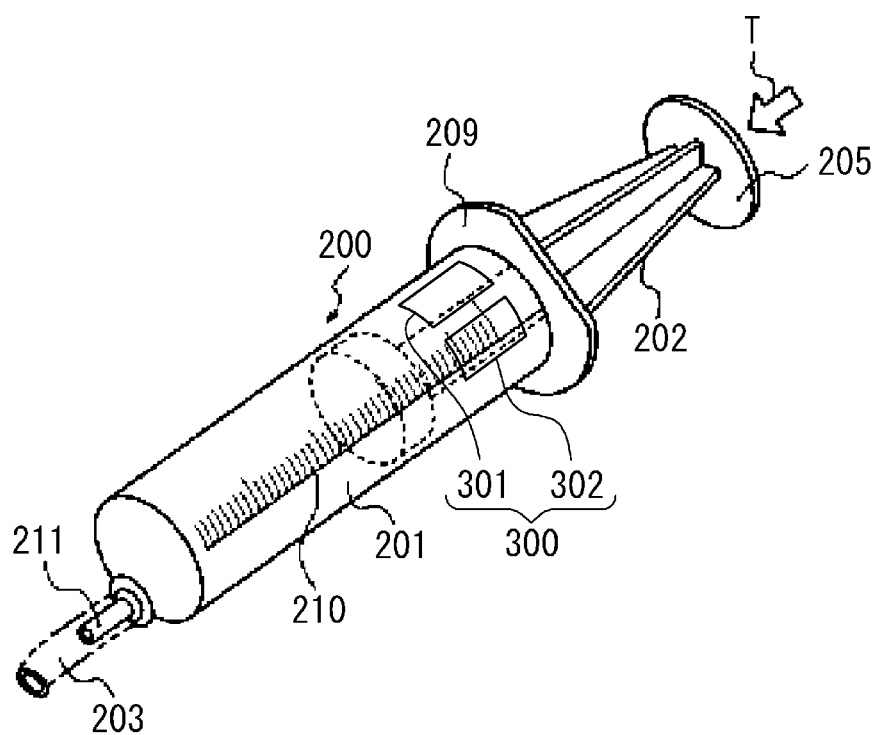
FIG. 5 is a schematic perspective view of the syringe illustrated in FIG. 1.

FIG. 5 is an external perspective view of the syringe 200. The syringe 200 includes the syringe body 201 and the syringe pusher 202. The syringe body 201 has a main body flange 209. The syringe pusher 202 has a pusher flange 205. A drug scale 210 is formed in the syringe body 201. The syringe body 201 has an outlet portion 211 to which one end portion of the flexible tube 203 is detachably connected. In a case in which the syringe 200 is a prefilled syringe of which the syringe body 201 is filled with a drug in advance, the syringe 200 is provided to a medical institution in a state where a cap for sealing the opening of the outlet portion 211 is attached to the outlet portion 211 of the syringe body 201. Examples of the drug with which the syringe body 201 is previously filled include intravenous anesthetics such as propofol, midazolam, and remifentanil, and vasoactive agents such as epinephrine, noradrenaline, dobutamine, dopamine, isosorbide nitrate, and nitroglycerin.

It is assumed that the syringe 200 is a prefilled syringe. The syringe 200 is provided to a medical institution in a state where the first RF tag 301 storing identification information including drug identification information corresponding to a drug with which the syringe body 201 is filled is attached to the syringe body 201 in advance. In the medical institution, the second RF tag 302 storing a unique code corresponding to the prescription information input by the doctor may be further attached to the syringe 200 to which the first RF tag 301 is attached.

Figure 6:
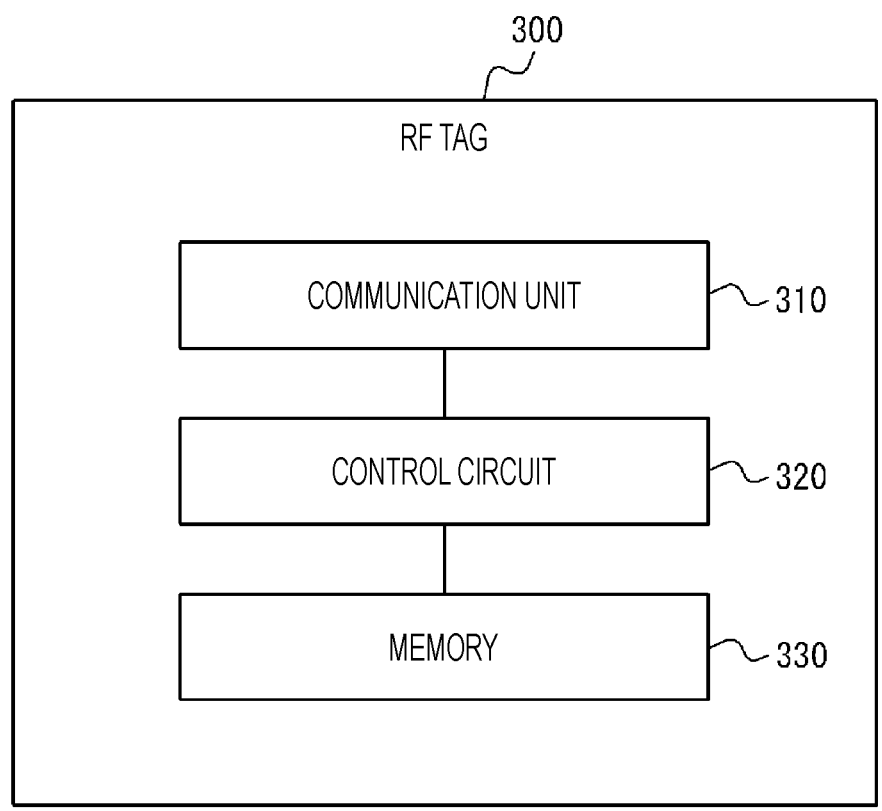
FIG. 6 is a schematic configuration diagram of an RF tag illustrated in FIG. 1.

FIG. 6 illustrates a schematic configuration diagram of the RF tag 300. As described above, the RF tag 300 includes a communication unit 310, a control circuit 320, and a memory 330.

The communication unit 310 performs wireless communication with a reader 170 (see FIG. 9) included in the medical infusion pump 100. The communication unit 310 communicates with the reader 170 by short-distance wireless communication using a frequency in an ultra high frequency (UHF) band or a high frequency (HF) band, for example.

The control circuit 320 controls the entire RF tag 300. When the communication unit 310 receives the request for transmission of the identification information from the reader 170 of the medical infusion pump 100, the control circuit 320 returns the identification information stored in the memory 330.

The memory 330 is a storage device that stores identification information. The memory 330 may be mounted on the same IC chip as the control circuit 320. The memory 330 may include a non-rewritable region and a rewritable region. The identification information may be stored in a rewritable region. When the RF tag 300 is the first RF tag 301, the memory 330 may include the first type of identification information (standard code) uniquely set for an article such as a drug according to the standard. When the RF tag 300 is the second RF tag 302, the memory 330 may include the second type of identification information (unique code) uniquely set by the medical institution. The memory 330 may store information other than the identification information.

As described above, when receiving the request for transmission of the identification information from the medical infusion pump 100 via the communication unit 310, the control circuit 320 transmits the identification information stored in the memory 330 to the medical infusion pump 100.

For example, in a case in which the RF tag 300 is used in the UHF band, the first RF tag 301 can adopt an identification code defined in the ISO/IEC 15459 standard as the identification information. ISO/IEC 15459 includes identification codes of ISO and GS1 forms. As an example, in a case in which the first RF tag 301 conforms to the GS1 EPC/RFID standard, the memory 330 stores information called an electronic product code (EPC). The standard to which the first RF tag 301 conforms is not limited to the above standard. The first RF tag 301 may adopt an RF tag according to various standards.

Figure 7:
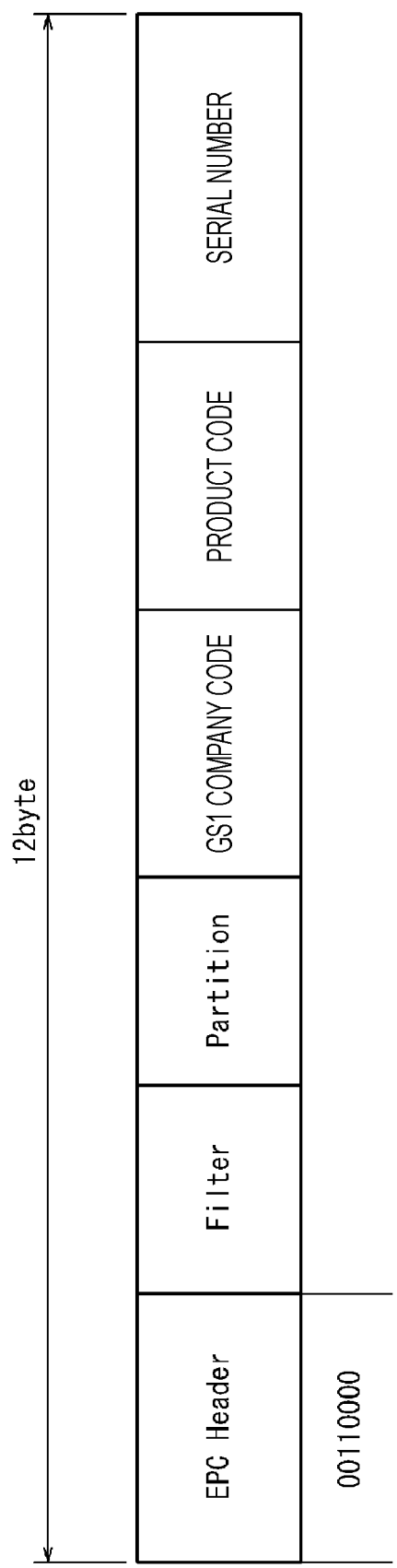
FIG. 7 is a diagram illustrating an example of a data structure of a standard code (first type of identification information).

FIG. 7 is a diagram illustrating an example of a data structure of SGTIN which is a standard code according to the GS1 EPC/RFID standard. The SGTIN is used as identification information used to identify individual products such as consumer goods and pharmaceuticals.

Because the data structure of SGTIN in FIG. 7 is known, only part thereof will be briefly described below. In FIG. 7, "EPC Header" is an 8-bit region representing the type of the EPC standard code. For SGTIN, the EPC Header is 00110000. The EPC standard code includes various standard codes such as a serial shipping container code (SSCC) and a global returnable asset identifier (GRAI) in addition to SGTIN. The value of the bit string of "EPC Header" is different according to each standard code. The "GS1 company code" is a region in which a code indicating a company is stored. The GS1 company code can be obtained from GS1 Japan in Japan. The "product code" is a region in which a code indicating a product is stored. A product identification code (GTIN: Global Trade Item Number) of the prefilled syringe is stored using the "GS1 company code" and the "product code". Therefore, the "GS1 company code" and the "product code" are drug identification information that can identify a drug.

Figure 8:
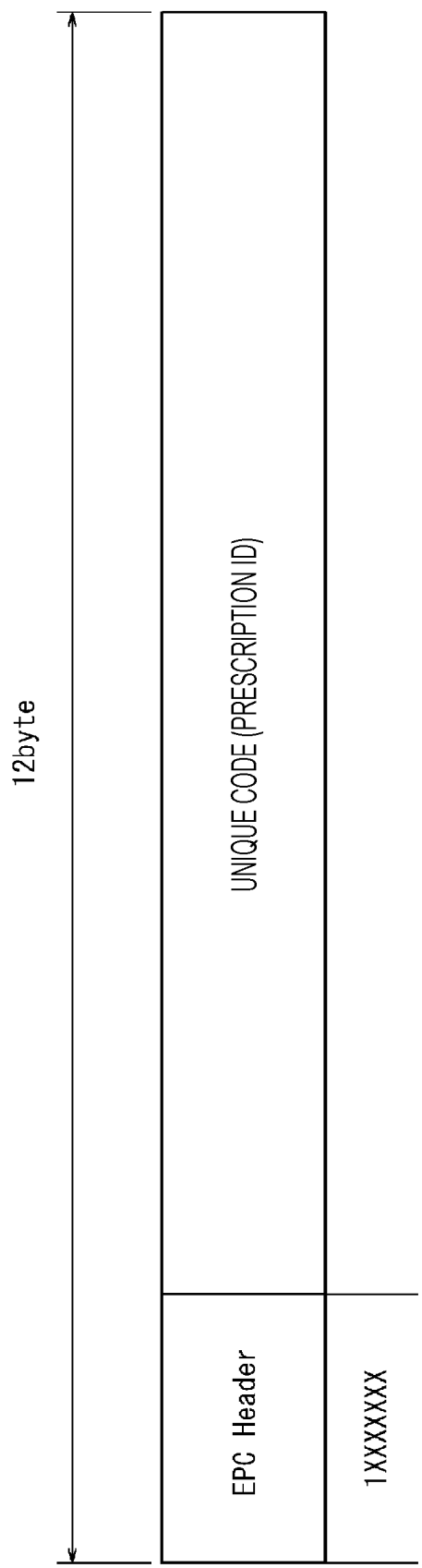
FIG. 8 is a diagram illustrating an example of a data structure of a unique code (second type of identification information).

The second RF tag 302 can be the same RF tag as the first RF tag 301 except for information stored in the memory 330. FIG. 8 is a diagram illustrating an example of a data structure of a unique code that is the second type of identification information stored in the second RF tag 302. The second type of identification information is different from the first type of identification information in data structure. In the second RF tag 302 illustrated in FIG. 8, a bit string other than the bit string indicating the type of the EPC standard code is disposed in the region of "EPC Header". For example, by setting the first one bit of the "EPC Header" to 1, a difference from the "EPC Header" of the standard code can be provided. In the second RF tag 302, a region following the "EPC Header" region of the memory 330 can be a region for storing a unique code. The region in which the unique code of FIG. 8 is stored can further have a unique data structure.

The medical infusion pump 100 can determine whether the identification information is a standard code or a unique code of a medical institution by referring to the "EPC Header" of the identification information received from the RF tag 300.

A device configuration of the medical infusion pump 100 will be described with reference to FIGS. 3 and 4 again.

The syringe installation unit 6 includes an accommodation unit 8 that houses the syringe body 201 and a clamp 5. The accommodation unit 8 is a recess having a substantially semicircular cross section in order to house the syringe body 201, and is formed along the X direction. The accommodation unit 8 has at a wall portion of its end portion a tube fixing unit 9 for detachably sandwiching the tube 203.

When the syringe 200 is removed from the syringe installation unit 6 by operating the clamp 5, the clamp 5 is pulled in the Y1 direction (forward direction) against the force of a spring (not illustrated) and further rotated by 90 degrees in the R1 direction. By this operation, the fixing of the syringe body 201 by the clamp 5 is released, and the syringe 200 can be removed from the accommodation unit 8. In addition, when the syringe 200 is attached to the syringe installation unit 6 by operating the clamp 5, the clamp 5 is pulled in the Y1 direction against the force of a spring (not illustrated), rotated by 90 degrees in the R2 direction, and returned in the Y2 direction by the force of the spring. By this operation, the syringe body 201 can be housed in the accommodation unit 8 and fixed by the clamp 5. The right end portion 8E of the accommodation unit 8 of the syringe installation unit 6 has partially a cutout portion so that the clamp 5 can fix the syringe 200 with various storing volumes such as 5 mL, 10 mL, 20 mL, 30 mL, and 50 mL.

When the syringe body 201 is housed and fixed in the accommodation unit 8, the syringe pusher 202 is disposed in the syringe pusher drive unit 7. The syringe pusher drive unit 7 includes a slider 10. The slider 10 presses the pusher flange 205 of the syringe pusher 202 little by little in the T direction relative to the syringe body 201 in accordance with a command from a control unit 180 illustrated in FIG. 9.

The X direction, the Y direction, and the Z direction in FIGS. 3 and 4 are orthogonal to each other. The Z direction is a vertical direction.

Next, an electrical configuration example of the medical infusion pump 100 illustrated in FIG. 1 will be described in detail with reference to FIG. 9.

Figure 9:
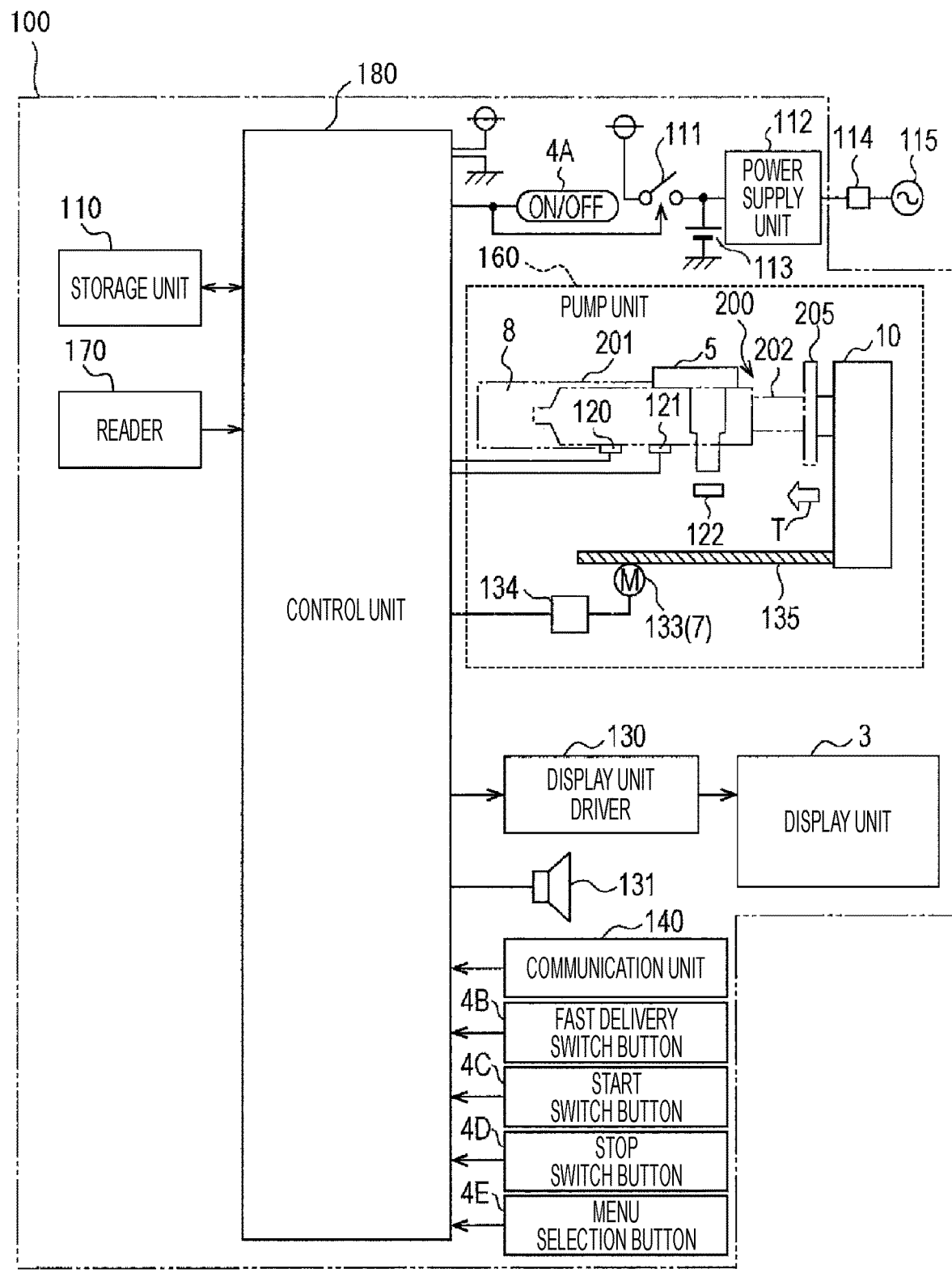
FIG. 9 is a schematic view illustrating an electrical configuration of a medical infusion pump illustrated in FIG. 1.

In FIG. 9, the medical infusion pump 100 includes the control unit (computer) 180 that determines and controls the overall operation. The control unit 180 is, for example, a one-chip microcomputer.

A power ON/OFF button 4A and a switch 111 are connected to the control unit 180.

Switch 111 switches between a power source converter unit (power supply unit) 112 and a rechargeable battery 113 such as a lithium ion battery to supply power from one of the power source converter unit 112 and the rechargeable battery 113 to the control unit 180.

The power source converter unit 112 is connected to a commercial AC power supply 115 via an outlet 114.

In FIG. 9, a pump unit 160 is electrically connected to the control unit 180. According to a command from the control unit 180, the pump unit 160 administers a drug to a patient according to information about administration of the drug. The information about administration of the drug includes at least one or more of a dose of a drug, an administration rate, an administration time, and an upper limit value and a lower limit value of the administration rate. The information about administration of the drug is set on the basis of at least any of the prescription information acquired from the server 410 and the drug profile of the drug library stored in the server 410 or the storage unit 110.

In FIG. 9, a pair of detection switches 120 and 121 is disposed in the accommodation unit 8 of the pump unit 160. The detection switches 120 and 121 detect whether the syringe body 201 of the syringe 200 is correctly disposed in the accommodation unit 8, and notify the control unit 180 of the result.

A clamp sensor 122 of the pump unit 160 detects the position state of the clamp 5 to notify the control unit 180 whether the syringe body 201 is reliably clamped by the clamp 5.

When driven by a motor driver 134 in accordance with a command from the control unit 180, a motor 133 of the syringe pusher drive unit 7 of the pump unit 160 rotates a feed screw 135 to move the slider 10 in the T direction. As a result, the slider 10 presses the pusher flange 205 of the syringe pusher 202 in the T direction, and accurately feeds the drug in the syringe body 201 illustrated in FIG. 4 to the patient P through the tube 203 via the indwelling needle 204.

In FIG. 9, a fast delivery switch button 4B, a start switch button 4C, a stop switch button 4D, and a menu selection button 4E are electrically connected to the control unit 180. When the start switch button 4C is pressed, a control signal for starting liquid delivery is input to the control unit 180. When the stop switch button 4D is pressed, a control signal for stopping liquid delivery is input to the control unit 180.

In FIG. 9, a display unit driver 130 is electrically connected to control unit 180. The display unit driver 130 drives the display unit 3 in accordance with a command from the control unit 180 to display various types of information on the display unit 3.

In FIG. 9, a notification unit 131 is electrically connected to the control unit 180. The notification unit 131 makes notification of various warning contents by voice, light, vibration, or the like according to a command from the control unit 180. In addition, in a case in which the control unit 180 makes notification of various warning contents by a display on the display unit 3, the display unit 3 may have a function as a notification unit.

A communication unit 140 may include at least one of wireless communication means and wired communication means. The communication unit 140 may be connected to a network such as a local area network (LAN) in the medical institution. The communication unit 140 communicates with the server 410 of the medical institution via a network. The control unit 180 may acquire the prescription information, the drug library, and the like from the server 410 via the communication unit 140. The communication unit 140 may transmit and receive data to and from the monitoring device 450 via a network. When an abnormality occurs in the medical infusion pump 100, the control unit 180 may notify the monitoring device 450 of the abnormality via the communication unit 140. Furthermore, the communication unit 140 may be locally connected to a computer such as a desktop computer to transmit and receive data.

The reader 170 communicates with the communication unit 310 of the RF tag 300 attached to the syringe 200 by wireless communication. The reader 170 can communicate with the plurality of RF tags 300.

When the syringe 200 is attached to the medical infusion pump 100, the reader 170 transmits a request for transmission of identification information to the RF tag 300. The reader 170 acquires the identification information transmitted from the RF tag 300 in response to the transmission request from the reader 170. In a case in which the syringe 200 has the first RF tag 301 and the second RF tag 302, the reader 170 acquires identification information from each of the first RF tag 301 and the second RF tag 302.

The control unit 180 determines whether the identification information is the first type of identification information uniquely defined according to the standard or the second type of identification information uniquely set by the medical institution on the basis of the data of the predetermined region of the identification information acquired by the reader 170.

A storage unit 110 may include, for example, a semiconductor memory, a magnetic memory, or the like. The storage unit 110 stores various types of information and programs necessary for the operation of the medical infusion pump 100.

The storage unit 110 may store a drug library including a plurality of drug profiles. The storage unit 110 can store a drug library customized by the medical institution possessing the medical infusion pump 100. For example, when the control unit 180 downloads the drug library stored in the server 410 of the medical institution to the storage unit 110 via the communication unit 140, the storage unit 110 can store the drug library customized by the medical institution.

When the syringe 200 is attached to the medical infusion pump 100 and the reader 170 acquires the first type of identification information from the RF tag 300, the control unit 180 identifies a drug from the standard code included in the identification information. For example, in a case in which the first type of identification information is a GSTIN standard code according to the SG1 EPC/RFID standard illustrated in FIG. 7, the control unit 180 can identify a drug using the "GS1 company code" and the "product code" as drug identification information.

In a case in which acquiring only the first type of identification information, the control unit 180 can execute the following processing.

The control unit 180 determines whether a drug profile corresponding to the acquired drug identification information is stored in the storage unit 110, and reads information of the drug profile in a case in which the drug profile is stored. As described above, the drug profile includes a reference administration rate and an upper limit value/a lower limit value of the administration rate.

When the syringe 200 is attached to the medical infusion pump 100, the control unit 180 can display the reference administration rate on the display unit 3 as an initial setting value of the administration rate. When the user such as a nurse sets the administration rate and the administration rate exceeds the upper limit value or falls below the lower limit value of the administration rate defined in the drug profile, the control unit 180 can cause the notification unit 131 to make notification of a warning. In a case in which the display unit 3 functions as a notification unit, the control unit 180 may make notification of a warning by changing the display of the display unit 3. In addition, in a case in which the administration rate is changed by the user during administration of the drug, and thus the administration rate exceeds the upper limit value or falls below the lower limit value, the control unit 180 causes the notification unit 131 to make notification of a warning. Accordingly, the medical infusion pump 100 can deter the user from administering the drug at an administration rate larger than the upper limit value or smaller than the lower limit value of the administration rate defined in the drug profile.

When the syringe 200 is attached to the medical infusion pump 100 and the reader 170 acquires one or two pieces of identification information including the second type of identification information from the RF tag 300, the control unit 180 can execute the following processing.

The control unit 180 acquires the prescription information associated with the unique code from the server 410 on the basis of the unique code included in the acquired second type of identification information. As described above, the prescription information includes patient identification information, drug identification information, and information such as a dose of a drug, an administration rate, and an administration time. The control unit 180 can display the patient name on the display unit 3 on the basis of the patient identification information. The control unit 180 can display, on the display unit 3, setting values such as a dose of a drug, an administration rate, and an administration time included in the prescription information. These setting values can be set as information about administration of the drug as they are after the user performs confirmation. As a result, the medical infusion pump 100 can reduce the possibility that the user erroneously sets the setting value related to the administration of the drug.

As in the case in which only the first type of identification information is acquired, the control unit 180 may determine whether a drug profile corresponding to drug identification information is stored in the storage unit 110, and read information of the drug profile in a case in which the drug profile is stored. In addition, in a case in which it is not stored, it may be acquired from the drug library stored in the server 410. As in the case in which only the first type of identification information is acquired, in a case in which the administration rate of the drug exceeds the upper limit value and falls below the lower limit value of the administration rate defined in the drug profile, the control unit 180 can cause the notification unit 131 to make notification of a warning.

In a case in which only the first type of identification information is acquired, the control unit 180 performs processing on the basis of only drug-specific information identified only by the drug identification information. On the other hand, when the second type of identification information is acquired, it is different from when only the first type of identification information is acquired in that the control unit 180 executes processing reflecting prescription information for an individual patient. In addition, the case in which the second type of identification information is acquired is different from the case in which only the first type of identification information is acquired in that more information can be associated with the drug with which the syringe 200 is to be filled.

On the basis of the identification information of the RF tag 300 attached to the syringe 200 attached to the medical infusion pump 100, the control unit 180 acquires part or all of the drug identification information, the drug profile, and the prescription information as the information about administration. The control unit 18 can reflect at least part of the information about administration in the display content of the display unit 3.

Figure 10:
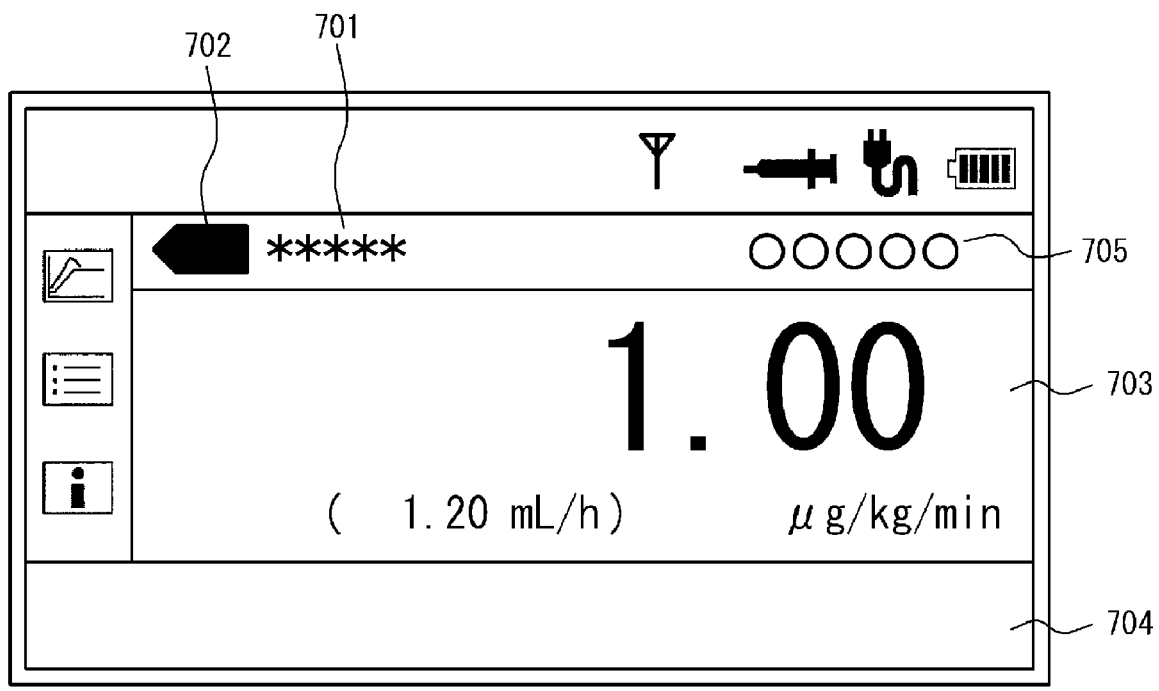
FIG. 10 is an example of display on a display unit of the medical infusion pump illustrated in FIG. 1.

FIG. 10 illustrates an example of a display on the display unit 3. In the example illustrated in FIG. 10, a drug name display field 701, a drug color display field 702, and an administration setting display field 703 are displayed. In a case in which there is a message, the message is displayed in a message field 704. Further, in a case in which the patient's name can be acquired, a patient name display field 705 is displayed.

In the drug name display field 701, a drug name such as "nitroglycerin" is displayed. In the drug color display field 702, a color set in advance corresponding to the drug is displayed.

In the administration setting display field 703, for example, the administration rate, the flow rate, and the like are displayed. In the example shown in FIG. 7, 1.00 [μg/kg/min] is displayed as the administration rate, and 1.20 [mL/h] is displayed as the flow rate.

In a case in which the control unit 180 reads the drug identification information, for example, a message such as "drug has been recognized" is displayed in the message field 704.

In a case in which the control unit 180 acquires the prescription information, the patient name is displayed in the patient name display field 705 on the basis of the patient identification information included in the prescription information.

When the start switch button 4C is pressed, the control unit 180 causes the pump unit 160 to administer the drug to the patient according to the set the information about administration of the drug.

Operation of Medical Infusion Pump System

Figure 11:
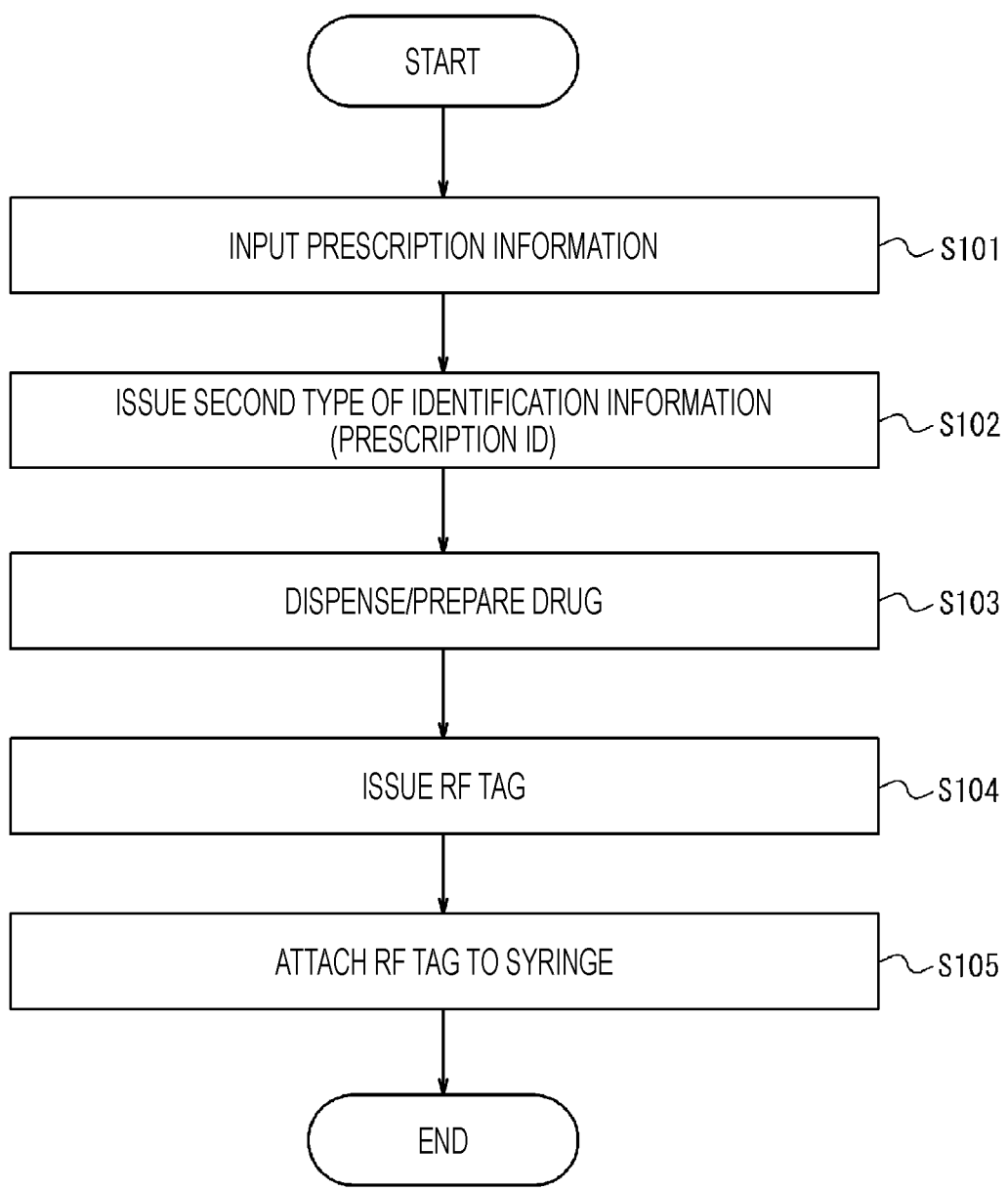
FIG. 11 is a flowchart illustrating an example of a procedure for attaching an RF tag including the second type of identification information to a syringe.

Hereinafter, the operation of the medical infusion pump system 1 will be described. First, a procedure for mounting the second RF tag 302 including the second type of identification information in the in-hospital system 400 on the syringe 200, which is a premise of the description of the operation of the medical infusion pump system 1, will be described with reference to FIGS. 2 and 11.

First, a doctor who has examined a patient inputs prescription information via the first information processing device 420 (step S101). The doctor inputs patient identification information, drug identification information such as a drug name, a dose of a drug, an administration rate, an administration time, and the like to the first information processing device 420. The prescription information input by the doctor is transmitted to the server 410.

The server 410 that has received the prescription information from the first information processing device 420 issues the second type of identification information and manages the received prescription information (step S102). The second type of identification information is, for example, a unique code such as a prescription ID represented by a non-overlapping number in a medical institution.

The prescription information is managed in the server 410 in association with the second type of identification information.

The prescription information is transmitted to the second information processing device 430 after undergoing a prescription audit as necessary. The second information processing device 430 is located, for example, in a pharmaceutical department in a medical institution. A pharmacist in the pharmaceutical department dispenses and/or prepares a drug on the basis of the prescription information presented to the second information processing device 430 (step S103). A drug with which a container such as a prefilled syringe is filled may be used as it is, or a drug may be prepared in a medical institution and the syringe 200 is filled with the drug. In some cases, the first RF tag 301 previously attached by a drug manufacturer is attached to the prefilled syringe.

Subsequent to the processing in step S103, the RF tag writer 440 issues the second RF tag 302 having the second type of identification information (step S104). The second RF tag 302 is issued by the RF tag writer 440 writing the second type of identification information in the memory 330 of the second RF tag 302 prepared in advance. The processing of step S104 may be performed before the processing of step S103. Alternatively, the processing of step S104 may be performed in parallel with the processing of step S103.

After steps S103 and S104, the second RF tag 302 issued in step S104 is attached to the syringe 200 including the prefilled syringe dispensed in step S103, the syringe filled with the dispensed drug, or the like (step S105). As described above, both the first RF tag 301 and the second RF tag 302, or only the second RF tag 302 is attached to the surface of the syringe 200.

Note that, in the present embodiment, the second RF tag 302 is not issued in step S104 and is not attached to the container in step S105 for some of the prefilled syringes. Therefore, only the first RF tag 301 may be attached to some syringes 200.

Figure 12:
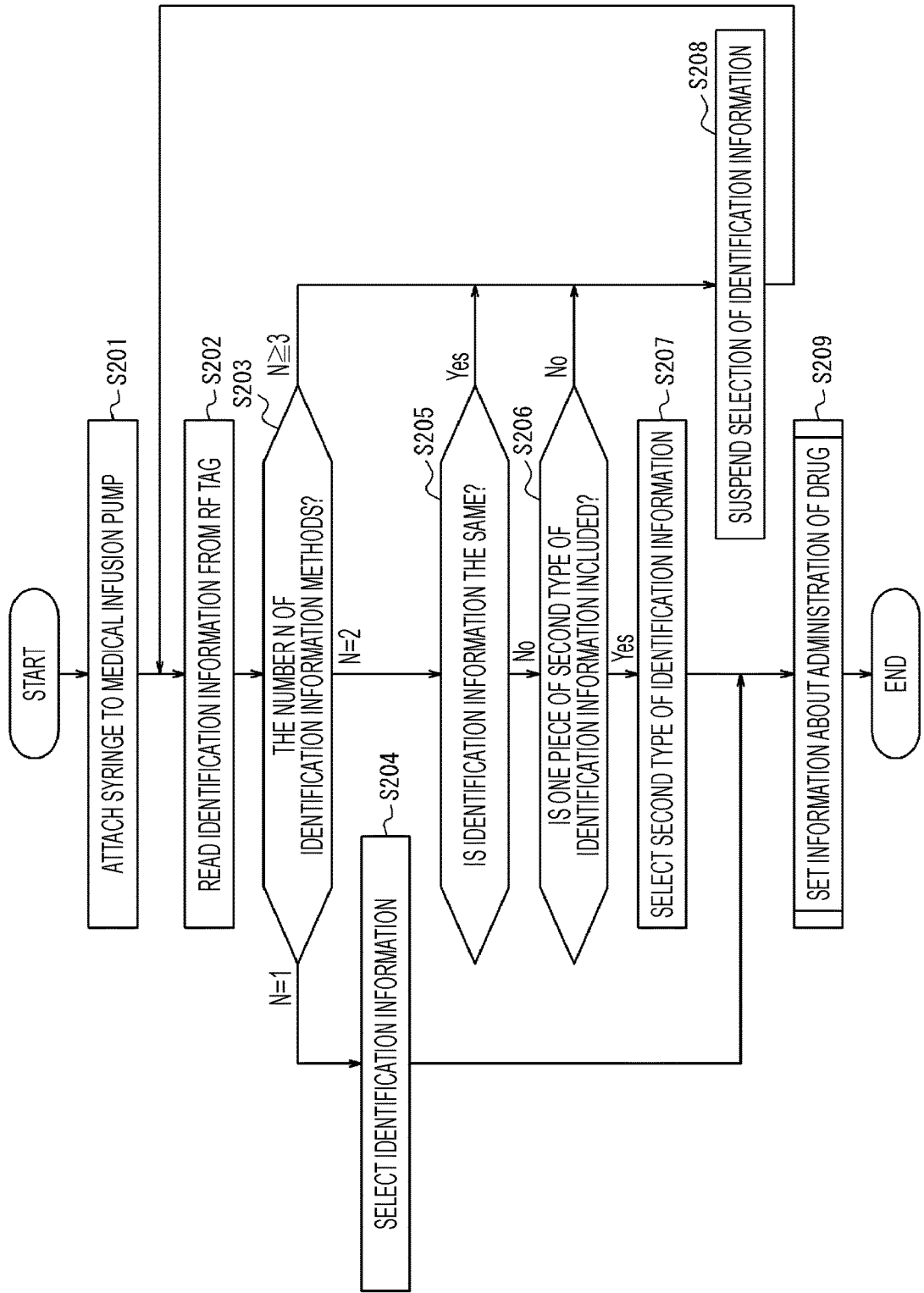
FIG. 12 is a flowchart illustrating an example of an operation of the medical infusion pump of FIG. 1.
Figure 13:
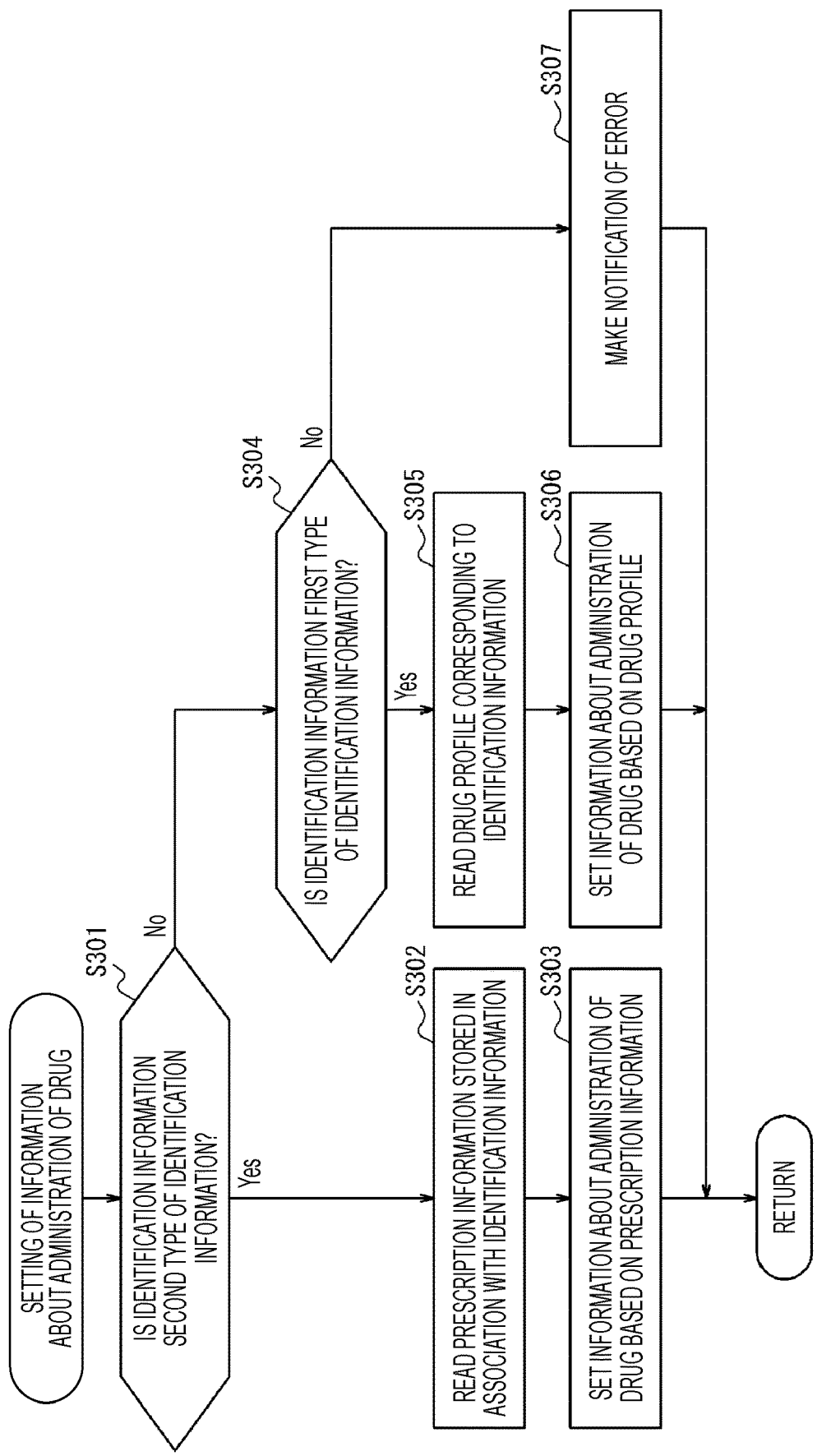
FIG. 13 is a flowchart illustrating an example of a procedure for setting information about administration of a drug to the medical infusion pump on the basis of identification information.

Next, the operation of the medical infusion pump 100 will be described with reference to the flowcharts of FIGS. 12 and 13.

First, a user such as a nurse attaches the syringe 200, which is a drug storage container, to the medical infusion pump 100 (step S201).

The reader 170 of the medical infusion pump 100 reads the identification information from the RF tag 300 attached to the syringe 200 (step S202). In a case in which a plurality of RF tags 300 is attached to the medical infusion pump 100, the reader 170 reads a plurality of pieces of identification information.

The control unit 180 of the medical infusion pump 100 performs the subsequent processing according to the number of pieces of identification information read by the reader 170 (step S203). The number of pieces of identification information read by the reader 170 is the same as the number of RF tags with which the reader 170 has communicated.

In a case in which the number of pieces of identification information read by the reader 170 is only one in step S203, the control unit 180 selects the one piece of identification information as identification information to be used for setting information about administration of a drug to the medical infusion pump 100 (step S204). The selected identification information may be first identification information acquired by the reader 170 from the first RF tag 301 or second identification information acquired by the reader 170 from the second RF tag 302.

In a case in which the number of pieces of identification information read by the reader 170 is two in step S203, the control unit 180 determines whether the two pieces of identification information are the same (step S205). The first identification information is a code uniquely assigned to the drug on the basis of the standard. The second identification information is a code allocated without duplication in the medical institution. Therefore, a case in which the two pieces of identification information are the same (step S205: Yes) means that some abnormality has occurred. For example, it is assumed that there is an error in allocating the same code to different RF tags 300. When the two pieces of identification information are different (step S205: No), the control unit 180 advances the process to the next step S206.

In step S206, the control unit 180 determines whether one piece of the second type of identification information is included in the two pieces of identification information read by the reader 170. When one of the two pieces of identification information is not the second type of identification information (step S206: No), it means that some abnormality has occurred. For example, it is assumed that the syringe 200 has only the first RF tag 301, but when reading the identification information, the reader 170 reads the identification information of the RF tag 300 of another syringe 200 located in proximity. In addition, it is assumed that a case in which both of the two pieces of identification information are the second type of identification information has some abnormality. In a case in which one of the two pieces of identification information is the second type of identification information (step S206: Yes), the control unit 180 advances the process to the next step S207.

In step S207, the control unit 180 selects the second type of identification information as identification information to be used for setting information about administration of a drug to the medical infusion pump 100 (step S207).

In a case in which the number of pieces of identification information read by the reader 170 is three or more in step S203, the control unit 180 suspends the selection of the identification information (step S208). That is, the control unit 180 does not determine the selection of the identification information and does not set the information about administration of the drug. Because up to two RF tags 300 are attached to the syringe 200, it is determined that the reader 170 reads three or more pieces of identification information due to some error. For example, the cause of such a situation is assumed to be a case in which the reader 170 erroneously reads an RF tag of another syringe located in proximity other than the syringe 200 attached to the medical infusion pump 100.

In addition, also in a case in which the two pieces of identification information are the same in step S205 (step S205: Yes) or in a case in which one piece of the second type of identification information is not included in step S206 (step S206: No), the control unit 180 suspends the selection of the identification information (step S208) and does not set the information about administration of the drug based on the identification information.

After step S208, the control unit 180 returns the process to step S202 and continues the processing. The control unit 180 repeats reading of the identification information from the RF tag 300 until the RF tag 300 attached to the syringe 200 can be normally read.

When the identification information to be used for control of the medical infusion pump 100 is selected in steps S204 and S207, the control unit 180 sets information about administration of a drug to the medical infusion pump 100 on the basis of the identification information (step S209). Hereinafter, processing of setting information about administration of a drug based on identification information will be described with reference to a flowchart of FIG. 13.

First, the control unit 180 determines whether the identification information is the second type of identification information (step S301).

When the identification information is the second type of identification information (step S301: Yes), the control unit 180 reads the prescription information stored in association with the second type of identification information from the server 410 (step S302). The read prescription information can be stored in the storage unit 110. The control unit 180 may acquire a drug profile, together with the prescription information, corresponding to the drug identification information from the drug library of the server 410 on the basis of the drug identification information included in the prescription information.

The control unit 180 sets information about administration of a drug according to the read prescription information (step S303). Specifically, the control unit 180 sets information such as a patient name, drug identification information, a dose of a drug, an administration rate, and an administration time defined in the prescription information as information about administration of the drug. Furthermore, the information about administration of the drug to be set may include information included in the drug profile of the drug identified by the drug identification information.

When the identification information is not the second type of identification information (step S301: No), the control unit 180 determines whether the identification information is the first type of identification information (step S304).

When the identification information is the first type of identification information (step S304: Yes), the control unit 180 acquires a drug profile corresponding to drug identification information included in the identification information from the storage unit 110 or the server 410 in the medical institution (step S305).

The control unit 180 sets information about administration of a drug according to the acquired drug profile (step S306). Specifically, the control unit 180 can display on the display unit 3 the reference administration rate defined in the drug profile as an initial setting value of the administration rate. In a case in which the administration rate exceeding the upper limit value defined in the drug profile or the administration rate falling below the lower limit value is set, the control unit 180 can issue an alarm by the notification unit 131.

When it is determined in step S304 that the identification information is not the first type of identification information (step S304: No), the control unit 180 causes the notification unit 131 to make notification of an error (step S307). The control unit 180 may return the process to a process of step S202 instead of notifying the error.

As described above, according to the medical infusion pump system 1 of the present disclosure, in a case in which the reader 170 reads two pieces of different identification information, the control unit 180 selects only one piece of identification information. As a result, even when the two RF tags 300 are attached to the syringe 200, it is possible to appropriately set the information about administration of the drug to the medical infusion pump 100.

In addition, according to the medical infusion pump system 1 of the present disclosure, the reader 170 can easily distinguish the first type of identification information allocated to the drug from the second type of identification information associated with the prescription information by referring to the data of the predetermined region of the information acquired from the RF tag 300. Therefore, the control unit 180 of the medical infusion pump 100 can perform processing according to the type of identification information.

Furthermore, when reading the identification information of the RF tag 300 attached to the syringe 200, the medical infusion pump system 1 of the present disclosure s recognizes, as an error, a case in which a plurality of pieces of the same identification information is read and a case in which three or more pieces of the identification information are read, and does not set the information about administration of the drug. As a result, it is possible to reduce the possibility of erroneous administration of a drug in a situation suspected of an error.

The medical infusion pump system 1 of the present disclosure can cope with both a case in which the first RF tag 301 having the first type of identification information is attached in advance to a prefilled syringe or the like and a case in which the second RF tag 302 uniquely having the second type of identification information is attached in a medical institution. In addition, because the control unit 180 of the medical infusion pump 100 preferentially adopts the second type of identification information over the first type of identification information, it is possible to set the prescription information associated with the prescription information of the patient and having a larger information amount as the information about administration of the drug.

Because the medical infusion pump system 1 of the present disclosure is configured to be able to acquire the prescription information from the server 410 via the communication unit 140, it is possible to cooperate with the prescription information created by the doctor and to reduce the capacity of the storage unit 132 of the medical infusion pump 100.

According to the medical infusion pump system 1 of the present disclosure, the medical infusion pump 100 reads the second type of identification information of the second RF tag 302 attached to the syringe 200. The medical infusion pump 100 acquires the prescription information associated with the second type of identification information from the server 410, and sets part or all of the prescription information as information about administration of a drug in the medical infusion pump 100. The information about administration of the drug set for the medical infusion pump 100 is at least partially displayed on the display unit 3 of the medical infusion pump 100. As a result, the doctor or the nurse who administers the drug by the medical infusion pump 100 can check information such as the patient to whom the drug is to be administered and the name of the drug. For example, the doctor or the nurse can confirm that the information identifying the individual, such as the registration card of the patient to whom the drug is to be administered, matches the name of the patient displayed on the display unit 3. For example, the doctor or the nurse carries the information terminal and can confirm that the prescription information read from the server 410 and the information displayed on the display unit 3 of the medical infusion pump 100 are consistent with each other.

Furthermore, in a case in which the reader 170 of the medical infusion pump 100 reads the second type of identification information of the second RF tag 302, acquires the prescription information from the reading server 410 and sets it for the medical infusion pump 100, the medical infusion pump 100 can be configured to set it as an initial value. As a result, it is possible to suppress the occurrence of an error such as the doctor or the nurse misreading the prescription information and mistaking a dose of a drug or an administration rate.

The present invention is not limited to the above-described embodiments, and various modifications can be made by those skilled in the art within the technical idea of the present invention. For example, the medical infusion pump is not limited to the syringe pump, and may be another type of medical infusion pump such as an infusion pump that delivers a drug contained in an infusion bag. In a case in which the medical infusion pump is an infusion pump, the infusion bag is a drug containing unit.

REFERENCE NUMERAL LIST 1 medical infusion pump system
2 main body cover
2A upper portion of main body cover
2B lower portion of main body cover
3 display unit
4 operation panel unit
4A power ON/OFF button
4B fast delivery switch button
4C start switch button
4D stop switch button
4E menu selection button
4F operation indicator
5 clamp
6 syringe installation unit
7 syringe pusher drive unit
8 accommodation unit
8E right end portion of accommodation unit
9 tube fixing unit
10 slider
100 medical infusion pump
110 storage unit
111 switch
112 power source converter unit (power supply unit)
113 rechargeable battery
114 outlet
115 commercial AC power supply
120 detection switch
121 detection switch
122 clamp sensor
130 display unit driver
131 notification unit
133 motor
134 motor driver
135 feed screw
140 communication unit
160 pump unit (adjustment mechanism)
170 reader
180 control unit
200 syringe (drug storage container)
201 syringe body
202 syringe pusher
203 tube
204 indwelling needle
205 pusher flange
209 main body flange
210 drug scale
211 outlet portion of syringe
300 RF tag
301 first RF tag
302 second RF tag
310 communication unit
320 control circuit
330 memory
400 in-medical institution system
410 server
420 first information processing device
430 second information processing device
440 RF tag writer
450 monitoring device
701 drug name display field of display unit
702 drug color display field of display unit
703 administration setting display field of display unit
704 message field of display unit
705 patient name display field of display unit
P patient

The invention claimed is:

1. A medical infusion pump comprising:
a reader configured to read identification information stored in an RF tag by wireless communication, wherein the identification information comprises a first type of identification information and a second type of identification information having different data structures; and
a control unit configured to, upon receiving the identification information and determining that the identification information comprises a first type of identification information and a second type of identification information having different data structures, select only one piece of the identification information out of the two different pieces of the identification information based on the data structure of said one piece of the identification information, and to set information about administration of a drug based on said one piece of the identification information.

2. The medical infusion pump according to claim 1, wherein the RF tag is attached to a drug storage container that contains the drug.

3. The medical infusion pump according to claim 2, wherein the drug storage container is a syringe.

4. The medical infusion pump according to claim 1, wherein the control unit is configured to select only said one piece of identification information based on data in a predetermined region of said data structure.

5. The medical infusion pump according to claim 1, wherein, the control unit is configured to, upon receiving the identification information and determining that the identification information comprises first identification information and second identification information that are the same, not set the information about administration.

6. The medical infusion pump according to claim 1, wherein the control unit is configured to, upon receiving the identification information and determining that the identification information comprises three or more pieces of identification information, not set the information about administration.

7. The medical infusion pump according to claim 1, wherein the control unit is configured to, upon receiving the identification information and determining that the identification information comprises only one piece of identification information, set the information about administration based on said one piece of identification information.

8. The medical infusion pump according to claim 1, further comprising a display unit configured to display the information about administration.

9. The medical infusion pump according to claim 1, wherein:
the first type of identification information is identification information allocated to the drug, and the second type of identification information is identification information associated with prescription information for administering the drug, and the control unit is configured to, upon receiving the identification information and determining that the identification information comprises a first type of identification information and a second type of identification information having different data structures, select only the second type of identification information based on the data structure of said second type of identification information, and to set the information about administration based on the second identification information.

10. The medical infusion pump according to claim 9, wherein the control unit sets at least part of the prescription information as the information about administration in a case in which the identification information includes the second type of identification information.

11. The medical infusion pump according to claim 9, further comprising a communication unit configured to communicate with a server, wherein the control unit is configured to acquire the prescription information stored in association with the second type of the identification information from the server via the communication unit.

12. The medical infusion pump according to claim 1, wherein:
the first type of identification information is identification information uniquely defined for the drug according to a standard, and the second type of identification information is identification information uniquely set by a medical institution, and
the control unit is configured to, upon receiving the identification information and determining that the identification information comprises a first type of identification information and a second type of identification information having different data structures, select only the second type of identification information based on the data structure of said second type of identification information, and to set the information about administration based on the second identification information.

13. The medical infusion pump according to claim 4, wherein the predetermined region is an electronic product code (EPC) header of the data structure.

14. A method of controlling a medical infusion pump, the method comprising:
reading identification information stored in an RF tag by wireless communication; and
upon receiving the identification information and determining that the identification information comprises a first type of identification information and a second type of identification information having different data structures, selecting one piece of the identification information out of the two different pieces of the identification information based on the data structure of said one piece of the identification information, and setting information about administration of a drug based on said one piece of the identification information.

15. A medical infusion pump system comprising:
a drug storage container to which an RF tag is attached; and
a medical infusion pump; wherein:
the drug storage container contains a drug to be administered to a patient;
the medical infusion pump comprises:
a reader configured to read identification information stored in the RF tag by wireless communication, and
a control unit configured to, upon receiving the identification information and determining that the identification information comprises a first type of identification information and a second type of identification information having different data structures, select only one piece of the identification information out of the two different pieces of the identification information based on the data structure of said one piece of the identification information, and to set information about administration of a drug based on said one piece of the identification information; wherein.

16. The medical infusion pump system according to claim 15, further comprising:
a server; wherein:
the medical infusion pump further comprises a communication unit configured to communicate with a server;
the server is configured to store information in association with the second type of identification information; and
the control unit is configured to select only the second type of identification information based on the data structure of said second type of identification information, to acquire the information stored in association with the second type of the identification information from the server via the communication unit, and to set the information about administration based on the information stored in association with the second type of the identification information.

* * * * *